United States Patent
Carlini et al.

(10) Patent No.: US 10,940,166 B2
(45) Date of Patent: Mar. 9, 2021

(54) BIOASSIMILABLE PROTEIN-MELANIN COMPLEX, PREPARATION AND USES

(71) Applicant: Rosanna Carlini, La Ciotat (FR)

(72) Inventors: Rosanna Carlini, La Ciotat (FR); Olivier Blanchardie, Toulon (FR); Jean-Sébastien Vella, Marseilles (FR)

(73) Assignee: Rosanna Carlini, La Ciotat (FR)

( * ) Notice: Subject to any disclaimer, the term of this patent is extended or adjusted under 35 U.S.C. 154(b) by 420 days.

(21) Appl. No.: 15/569,863

(22) PCT Filed: Apr. 29, 2016

(86) PCT No.: PCT/FR2016/051010
§ 371 (c)(1),
(2) Date: Oct. 27, 2017

(87) PCT Pub. No.: WO2016/174367
PCT Pub. Date: Nov. 3, 2016

(65) Prior Publication Data
US 2018/0110809 A1 Apr. 26, 2018

(30) Foreign Application Priority Data

Apr. 30, 2015 (FR) .................................. 1553920

(51) Int. Cl.
*A61K 35/36* (2015.01)
*A61K 38/02* (2006.01)
*A61K 8/64* (2006.01)
*A61Q 17/04* (2006.01)
*A61Q 19/08* (2006.01)
*A61K 8/98* (2006.01)
*A61K 31/404* (2006.01)
*A61K 8/72* (2006.01)
*A61K 8/65* (2006.01)
*A61P 43/00* (2006.01)
*A61K 31/435* (2006.01)

(52) U.S. Cl.
CPC ............... *A61K 35/36* (2013.01); *A61K 8/64* (2013.01); *A61K 8/65* (2013.01); *A61K 8/72* (2013.01); *A61K 8/985* (2013.01); *A61K 31/404* (2013.01); *A61K 31/435* (2013.01); *A61K 38/02* (2013.01); *A61P 43/00* (2018.01); *A61Q 17/04* (2013.01); *A61Q 19/08* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 6,315,988 B1 * | 11/2001 | Mani | A61K 8/37 424/59 |
| 2003/0096735 A1 * | 5/2003 | D'Amato | A61K 31/775 514/13.3 |

OTHER PUBLICATIONS

Liu et al. "Comparison of the structural and physical properties of human hair eumelanin following enzymatic or acid/base extraction", Pigment Cell Research, Munksgaard International Publishers, Cambridge, MA, DK, vol. 16, No. 4, Aug. 1, 2003 (Aug. 1, 2003), pp. 355-365.*
Golounin "Production of melanin useful in cosmetic and cancer—from human hair, horse hair or wool by alkali extraction an boiling", WPI World Patent INF, Jan. 1, 1998.*
Liu Yan et al.,"Comparison of the structural and physical properties of human hair eumelanin following enzymatic or acid/base extraction", Pigment Cell Research, pp. 355-365, vol. 16. No. 4 (Aug. 2003).
Golounin A. V., "Production of melanin useful in cosmetic and cancer—from human hair, horse hair or wool by alkali extraction an boiling", WPI World Patent INF, (Jan. 1998)—abstract.

* cited by examiner

*Primary Examiner* — Maury A Audet
(74) *Attorney, Agent, or Firm* — Browdy and Neimark, PLLC

(57) ABSTRACT

The present invention relates to a bioassimilable protein-melanin complex, advantageously soluble in water, comprising a protein extract, advantageously rich in S-sulfonated residues and melanin. The claimed complex further exhibits subsequent good assimilation in the human body. The invention also relates to a method for preparing the claimed bioassimilable protein-melanin complex, use of said complex and compositions containing at least said complex.

16 Claims, 5 Drawing Sheets

BIOASSIMILABLE PROTEIN-MELANIN COMPLEX, PREPARATION AND USES

The present invention relates to a bioactive bioassimilable protein-melanin complex, comprising a protein extract, advantageously at least partially soluble, and melanin. The complex according to the invention moreover has good subsequent assimilation in the human body. The invention also relates to a process for the preparation of said bioassimilable protein-melanin complex according to the invention, the use of said complex as well as compositions comprising at least said complex.

The melanins are complex biological polymers that are found in humans, animals, plants, bacteria, fungi and protists.

In man, melanins are present in the skin, hair, parts of the brain and parts of the eye and the ears.

Biological melanins are macromolecules produced mainly by the melanocytes, by the addition or condensation of monomers formed from tyrosine (eumelanin) or tyrosine and cysteine (pheomelanin), in association with tyrosinase (Plonka, P. M. and Grabacka, M.; *Melanin synthesis in microorganisms-biotechnological and medical aspects* Acta Biochimica Polonica 2006 53: 429-443).

Artificial melanins also exist such as polyacetylenes, polyanilines, and polypyrroles of black or brown colour, and theft copolymers; they have an industrial and/or biotechnological application.

In the present text and subject to a specific indication the terms "melanin" or "melanins" may be used indiscriminately to denote natural and/or artificial melanins, of whatever origin, alone or in a mixture, whether eumelanin, pheomelanin, or a mixture of the 2 in all proportions or also products which are synthesis intermediates, degradations thereof as well as optionally modified forms thereof.

In the structure of melanins, free radicals exist in equilibrium with non-radical groups.

The melanins are very resistant to decay and to biodegradation.

The melanins have strong antioxidant properties and can protect against attacks by lytic enzymes.

The melanins have radioprotective properties due to their ability to absorb radionuclides effectively.

The melanins can contribute to the reduction of excess heavy metals in the human body.

The melanins are well-known for effectively protecting living organisms from ultraviolet (UV) radiation.

The therapeutic potential of the melanins for applications in medicine, pharmacology, cosmetics, in all compatible forms such as pharmaceutical and/or cosmetic compositions, or also nutritional supplements, is well documented (Plonka, P. M. and Grabacka M., op. cit.).

The melanins play an important role in photoprotection, particularly of the human skin, against the acute effects of exposure to UV (for example sunburn), such as the potential long term risks of actinic changes (wrinkles and premature ageing of the skin) and of precancerous or malignant states (solar keratosis, basal cell carcinomas and/or squamous cell carcinomas, malignant tumours).

The melanins (principally eumelanin) are present in the epidermis in a particulate form, melanosome, and in an amorphous form, colloidal melanins, and through these forms offer protection to the cells.

In addition to the skin, the melanins are also present in the retinal pigment epithelium (RPE) of the human eye. The melanins of the RPE, principally eumelanin, play a photoprotective role by absorption of the radiation and by trapping the reactive free radicals and the reactive oxygen species (ROS).

A phototoxic role of the melanins of the RPE, in particular in aged cells, including the increased photogeneration of ROS such as the superoxide anions and the hydroxyl radicals that are involved in RPE cell death has also been described.

The chemistry of the melanins is of particular interest because RPE cell death is a major characteristic of the pathogenesis of age-related macular degeneration (ARMD), main cause of blindness in the human population over 60 years of age in the developed world (Brandon-Luke, L. et al. *Time Resolved Detection of Melanin Free Radicals Quenching Reactive Oxygen Species* J. Am. Chem. Soc. 2005 127, 11220-1221).

In order to identify the means for further exploiting the functionalities of the melanins and allow their potential biotechnological applications to emerge, emphasis has been placed on the aqueous solubilization of melanins.

Soluble melanins can be produced by synthesis or isolated from natural sources (U.S. Pat. Nos. 5,216,116; 5,218,079; 5,225,435; 5,227,459; 5,384,116; 5,574,125; 6,315,988; 5,814,495; 6,576,268).

Although a great many studies have been done on the synthesis of synthetic melanins and the production of melanin from bacteria or plant sources such as legumes and fruits, the production of melanins from mammals has remained largely undeveloped, because the melanins from mammals are very insoluble and require harsh treatments such as boiling in a strong basic medium, or the use of strong oxidants such as hydrogen peroxide, which leads to damage and denatures the melanins produced as well as the protein complexes surrounding said melanins.

Many studies have been carried out on the natural melanins obtained from plants or from bacterial sources later rendered soluble in water. These studies have lead to multiple topical applications of the melanins in cosmetics and dermatology, which has in fact made it possible to note a certain cutaneous absorption of melanins.

The interest in biological and therapeutic roles of the melanins on the human body is increasing, but little work has really been carried out with the aim of obtaining a melanin that is really bioassimilable by the human body, particularly when the melanins are of animal origin, particularly from mammals.

Therefore a real need exists for melanins that are bioassimilable or rendered bioassimilable, particularly for melanins of animal origin, more particularly of mammalian origin, that are bioassimilable or rendered bioassimilable, said melanins having in addition retained their intrinsic properties, particularly biological properties, and therefore able to be characterized as active or bioactive melanins. One of the aims of the present invention is to propose a melanin, advantageously of animal origin, mammalian or avian, preferentially mammalian, that is bioassimilable or rendered bioassimilable, easy to prepare, and has properties that can be used in both humans and animals in the fields of cosmetics, dermatology, pharmaceuticals or food, as a result of retaining its intrinsic properties, particularly biological properties.

The work of the applicant has in fact led him to the development of a protein-melanin complex having the property of being bioassimilable and offering a melanin that has retained its intrinsic properties, particularly biological properties, and is capable of expressing them once introduced into the organism of the receiver (bioactive melanin). Thus, it will be possible moreover in the present text to qualify the protein-melanin complex which is the subject-matter of the invention as bioassimilable and/or bioactive.

According to the present invention by "complex" is meant a combination of molecules, more or less intimately bound together.

In the particular case of the present invention, said protein-melanin complex should be understood as being able at least to comprise a protein extract and melanin more or less intimately bound together.

By "bioassimilable" is meant, according to the present invention, the ability of a molecule or a composition, to pass through the biological barriers, such as the skin including the scalp, or also the gastro-intestinal barrier, and to end up available in the circulation, advantageously without being degraded, partially or totally, or eliminated.

Therefore a first subject of the invention is a bioassimilable protein-melanin complex, being able to comprise at least one protein extract, soluble or partially soluble and melanin, said protein-melanin complex being able to be advantageously bioactive and said protein extract comprising at least one cysteine residue or at least one tyrosine residue or at least one cysteine residue and one tyrosine residue.

By "protein extract" is meant according to the invention that said protein-melanin complex according to the invention may comprise proteins and/or protein fragments (peptides) originating from the protein source or from the retained melanoprotein source. By "melanoprotein source" is meant in this case a single source that contains both proteins and melanin.

By "soluble or partially soluble protein extract" is meant according to the invention that the proteins and/or the protein fragments (peptides) present in said extract have been rendered soluble by any solubilization technique of the proteins and/or of the protein fragments (peptides) known to a person skilled in the art, such as for example hydrolysis or a chemical modification. By way of chemical modification, the grafting of polar groups on said proteins and/or protein fragments (peptides), particularly on the cysteines of said proteins and/or of said protein fragments (peptides), very particularly on the sulphur atom of said cysteines, may be mentioned as examples.

By "cysteine" is meant according to the invention cysteine as such, free or involved in a peptide bond, or also cystine.

According to the invention, the proteins and/or the protein fragments (peptides) may have been rendered soluble by the grafting of at least one polar group, particularly on at least one cysteine of said proteins and/or of said of a polar group, advantageously selected from the phosphate, sulphate or sulphite groups, preferentially sulphite. Of course when the grafting of several groups is used, the grafted groups can be identical or different in all possible combinations.

According to a particularly preferred form of the invention the soluble or partially soluble protein extract present in said protein-melanin complex may comprise at least one cysteine bearing a sulphite group on its sulphur atom, moreover called S-sulphonated cysteine or S-sulphocysteine in the present text.

Advantageously according to the invention said soluble or partially soluble protein extract present in said protein-melanin complex may comprise between one and all its cysteines in the form of S-sulphonated cysteines, very advantageously between a third and all, yet more preferentially between a half and all of its cysteines in the form of S-sulphonated cysteines. According to a very preferred form of the invention said soluble or partially soluble protein extract present in said protein-melanin complex may comprise 100% of its cysteines in the form of S-sulphonated cysteines.

According to the invention, said protein extract may be soluble in water from 0.1 to 99%, preferentially from 0.1 to 75%, very preferentially from 0.1 to 50%. The solubility can be measured using an HI 83703 turbidity meter from HANNA Instruments (designed according to the ISO 7027 standards of the international FTU (Formazine Turbidity Unit) standard equivalent to the NTU (Nephelometric Turbidity Unit) and intended to measure turbidity very precisely. The lower the turbidity, the more soluble the sample; the higher the turbidity, the more microparticles and insoluble bodies there are in the medium.

At a concentration comprised between 3 and 10% in water, said protein or protein-melanin extract of interest has an extremely low or even zero turbidity, from 0.00 to 50 NTU. Said protein or protein-melanin extract of interest can be soluble, so that it can pass through 5 to 100 µm porosity filters without being retained. The soluble extract of interest can represent more than 50% of the yield with respect to the protein or melanoprotein weight originating from the raw material used, determined by dry weight before and after filtration.

According to the invention, said protein-melanin complex may comprise from 0.01% to 99.99% of protein extract, preferentially between 1% and 95%, very preferentially between 30% and 95%, yet more preferentially between 50% and 95%.

According to the invention, said protein-melanin complex may comprise from 0.01% to 99.99% of melanin, preferentially between 0.5% and 20%, very preferentially between 1% and 15%.

According to the invention, said protein extract may comprise between 0.1% and 100% of protein fragments (peptides), preferentially between 30% and 100%, very preferentially between 55% and 100% of protein fragments (peptides).

According to the invention, said protein fragments (peptides) may have a length comprised between 2 and 1,000 amino acids, preferentially between 2 and 500 amino acids, very preferentially between 2 and 100 amino acids.

According to a variant of the invention said protein extract and said melanin may originate from different or identical protein and melanin sources, taken separately.

According to another preferred variant of the invention, said protein extract and said melanin can originate from one and the same melanoprotein source, advantageously used alone.

It will be noted that according to the invention, both the melanin source and the protein source and the melanoprotein source can be single sources or a mixture of different melanin, protein or melanoprotein sources, in any proportions.

Thus, according to the invention the melanin and/or the protein extract can originate from
    a single melanin source and a single protein source;
    a mixture of melanin sources and a single protein source;
    a mixture of melanin sources and a single protein source and a single melanoprotein source;
    a mixture of melanin sources and a single protein source and a mixture of melanoprotein sources;
    a single melanin source and a mixture of protein sources;
    a single melanin source and a mixture of protein sources and a single melanoprotein source;

a single melanin source and a mixture of protein sources and a mixture of protein-melanin sources;

a mixture of melanin sources and a mixture of protein sources;

a mixture of melanin sources and a mixture of protein sources and a single melanoprotein source;

a mixture of melanin sources and a mixture of protein sources and a mixture of melanoprotein sources;

a single melanoprotein source;

a single melanoprotein source and a single melanin source;

a single melanoprotein source and a single protein source;

a mixture of melanoprotein sources and a single melanin source;

a mixture of melanoprotein sources and a single protein source.

According to the invention, the melanin source may be synthetic, semi-synthetic or obtained by extraction from a natural source. Preferably a melanin of natural extraction will be used. The natural melanin source can be of animal origin, including human; plant, fungal, or micro-organic, preferentially of animal origin, including human; very preferentially of mammalian or avian origin, yet more preferentially of mammalian origin.

Thus, as a natural melanin source that can be used according to the invention, the melanin originating from wool, bristles, hair, claws, horns or also feathers, plants, fruits, the ink from cephalopods, bacteria or synthetic sources can be mentioned as examples Preferentially, the melanin source may be wool such as that from sheep, mouflons, goats, chamois, takin, ibexes, Siberian ibexes, thars, Himalayan thars, serows, goral, musk ox, urial, bharal, isard, rabbits, hares, pikas, llama, alpaca, guanaco, vicuna, camel, dromedary, yak or feathers such as that from magpie, crow or blackbird. A preferred wool can be sheep's wool, particularly from black sheep (such as for example those of the breeds "Ouessant", "Noire du Velay", "Valais Blacknose", "Noir de Thibar", "Black Welsh Mountain", "Balwen", "Zwartbles" or also "Hebridean" sheep), very precisely the wool from sheep of the "Noire du Velay" breed.

A person skilled in the art would have understood that in the present text the term "sheep" (*Ovis acres*) is used to denote a herbivorous domestic mammal of the family of the bovids, of the sub-family of the Caprinae and of the genus *Ovis*. The term also covers the young animal (lamb/young ewe), the female (ewe) the male (ram), castrated or uncastrated.

Examples of derivatives of synthetic melanin that can be used are described in patent application U.S. Pat. Nos. 5,618,519, 5,384,116, and 5,227,459. Examples of derivatives of soluble melanin that can be used are described in patent application U.S. Pat. Nos. 5,744,125, 5,225,435, 5,218,079, and 5,216,116. Examples of derivatives of commercial soluble melanin that can be used are for example Melasyn-100™ from San-mar laboratories, Inc. (Elmsford, N.Y. USA) and MelanZe™ from Zylepsis (Ashford, Kent, Great Britain).

According to the invention, said protein extract can originate from any natural or synthetic protein source, preferentially natural. Said natural protein source can be of any origin and in any form. Preferentially it may be of animal or plant, fungal, or micro-organic origin, advantageously of animal or plant origin, preferentially animal, very preferentially of mammalian or avian origin, yet more preferentially of mammalian origin.

According to a preferred form of the invention, the protein source may be an animal source, preferentially a protein source comprising keratin such as for example the keratinized appendages of many animals, advantageously of mammals including man, among which there can be mentioned the bristles, hair, whiskers, wool, feathers, horns, nails, claws, hooves, beaks, scales.

It is understood from the foregoing that when according to the invention a melanoprotein source is used this can be of any origin provided that it contains both proteins and melanin. According to the invention, the melanoprotein source may be of animal, plant, fungal, or micro-organic origin, advantageously of animal origin, advantageously from mammals including man, very advantageously the keratinized appendages, among which there can be mentioned the bristles, hair, whiskers, wool, feathers, horns, nails, claws, hooves, beaks, scales.

Preferentially according to the invention, said melanoprotein source may be wool, such as that from sheep, mouflons, goats, chamois, takin, ibexes, Siberian ibexes, thars, Himalayan thars, serows, goral, musk ox, urial, bharal, isard, rabbits, hares, pikas, llama, alpaca, guanaco, vicuna, camel, dromedary, yak or feathers such as those from magpie, crow or blackbird. A preferred wool can be sheep's wool, particularly from black sheep (such as for example those of the breeds "Ouessant", "Noire du Velay", "Valais Blacknose", "Noir de Thibar", "Black Welsh Mountain", "Balwen", "Zwartbles" or also "Hebridean"), very precisely the wool from sheep of the "Noire du Velay" breed.

A preferred form of the bioassimilable protein-melanin complex according to the invention may be a complex the protein extract and the melanin of which may originate from one and the same melanoprotein source, advantageously from black wool, very advantageously from the black wool of sheep, particularly the black wool of sheep of the Noire du Velay" breed, being able to comprise from 0.01% to 99.99% of protein extract, preferentially between 1% and 95%, very preferentially between 30% and 95%, yet more preferentially between 50% and 95%, itself comprising from 0.1% to 100% of protein fragments (peptides), preferentially between 30% and 100%, very preferentially between 55% and 100%, the length of which may be comprised between 2 and 1,000 amino acids, preferentially between 2 and 500 amino acids, very preferentially between 2 and 100 amino acids, and 0.01% to 99.99% of melanin, preferentially between 0.5% and 20%, very preferentially between 1% and 15%, and being able to comprise between 10% and 100% of its cysteines in the form of S-sulphonated cysteines, very advantageously between 30% and 100%, yet more preferentially between 50% and 100% of its cysteines in the form of S-sulphonated cysteines, very preferentially said protein-melanin complex may comprise 100% of its cysteines in the form of S-sulphonated cysteines.

A subject of the invention is also a process for the preparation of said bioassimilable protein-melanin complex according to the invention, according to which in a first step the protein part of said protein or melanoprotein source is rendered solubilizable, advantageously water-solubilizable, in a second step the protein part of the mixture obtained in the first step is fractionated to peptides, in order to obtain a mixture comprising the sought protein-melanin complex.

In fact, according to a first embodiment of said process according to the invention, if the protein and melanin sources are physically different from one another according to the process according to the invention, in a first step the protein part of said solubilizable protein source is advantageously rendered water-solubilizable, in a second step the protein part of the mixture obtained in the first step is fractionated to peptides, in a third step the melanin is introduced into the mixture obtained in the second step, in order to obtain a mixture comprising the sought protein-melanin complex.

It should be noted that according to this process the introduction of the melanin can just as well take place before the first step intended to render the proteins solubilizable, which may then take place on a mixture of a protein source/melanin source which are physically different, after the first step, therefore before the second step of fractionating the proteins, which may then take place on a mixture of a protein source rendered solubilizable/melanin source, or after the second step by adding the melanin to the protein source mixture rendered solubilizable and fractionated. Preferentially according to the invention, in this embodiment of the process, the introduction of the melanin may be done after the second step.

According to a second embodiment of said process according to the invention, if the protein and melanin sources are physically identical (melanoprotein source) according to the process according to the invention in a first step the protein part of said melanoprotein source is rendered solubilizable, advantageously water-solubilizable, in a second step the protein part of the mixture obtained in the first step is fractionated to peptides, in order to obtain a mixture comprising the sought protein-melanin complex. It is understood that in this embodiment of the process the melanin is present from the first step.

In itself, each step of the process according to the invention can be carried out with techniques completely known to a person skilled in the art. The originality of the process developed by the inventors resides in bringing together the different steps, which makes it possible to end up with a bioassimilable protein-melanin complex, optionally soluble according to the pH conditions and which furthermore has properties that can be used in the cosmetic, dermatological, pharmaceutical or food fields.

According to the invention, said mixture obtained in the last step, comprising said protein-melanin complex according to the invention, can be used directly or undergo any conceivable step for its conversion to a product with a form more suitable for its subsequent utilizations.

According to the invention, the sources of proteins and melanins can be presented in any form compatible with the implementation of the process according to the invention. For example the proteins can be in the liquid, solid or semi-solid form [for example collagens, hydrolysates of collagen or gelatins, milk proteins, caseins, plant proteins (soya, wheat, rice etc.) in different forms (granules, solutions, straws, flakes, upgraded food waste etc.)]. The melanin can be in liquid, solid, semi-solid form, (such as for example powdered squid ink).

According to the invention, the first step intended to render the protein part of the mixture solubilizable, advantageously water-solubilizable, can be carried out by any methods known to a person skilled in the art such as for example the grafting of groups, advantageously polar (hydrophilic therefore soluble in water), capable of rendering said proteins or said peptides soluble, on said proteins or peptides or by rupture of the chemical bonds between the protein or peptide chains such as for example reduction of the disulphide bridges. For example, the reactions of grafting phosphate, sulphite or sulphate groups being able to be catalyzed chemically or enzymatically may be mentioned, which can be carried out by any methods known in the prior art such as for example phosphorylation, sulphatation, or also oxidative sulphitolysis, it being understood that the protein part of the mixture can be subjected to one or more of these consecutive or associated grafting reactions. Preferentially according to the invention, oxidative sulphitolysis may be used, which has the double feature of ending up with the grafting of sulphites, polar groups, on the side chains of the cysteine residues and also of cutting the disulphide bridges, releasing the protein chains from one another and promoting their solvation in water [Crewther W. G. et al., *The chemistry of keratins* in Advances in protein chemistry, Academic Press, vol. 20; 1965, pages 191-346; Otto Lindner, Lars Rodefeld, *Benzenesulphonic Acids and Their Derivatives*, Wiley-VCH Verlag GmbH & Co, coll. "Ullmann's Encyclopedia of Industrial Chemistry", 15 Sep. 2000; FR2521571 (19 Aug. 1983); U.S. Pat. No. 3,644,084 (1 Dec. 1971). Advantageously during this reaction the polar group(s), advantageously the sulphite(s) may be grafted on the cysteines of said proteins and/or of said protein fragments (peptides), very particularly on the sulphur atom of said cysteines.

According to the invention, the second step of hydrolysis can be carried out by any hydrolysis methods known in the prior art such as for example acid hydrolysis, basic hydrolysis or also enzymatic hydrolysis, preferentially enzymatic hydrolysis. It should be noted that this step can also be carried out by partial oxidation by using peracetic acid, hydrogen peroxide or an equivalent, under the conditions known to a person skilled in the art. Preferentially according to the invention, the second step of the process may be carried out by enzymatic hydrolysis according to the methods described in the literature relating to enzymatic protein hydrolysates such as for example Industrial Enzymes: Structure, Function and Applications (2007, Julio Polaina, Andrew P. MacCabe Ed., published by Springer).

According to a variant of the invention steps 1 and 2 can be reversed.

According to a variant of the invention, a step of enzymatic inactivation can be optionally carried out making it possible to guarantee the absence of any residual proteolytic activity. This optional inactivation step can be carried out just after step 2, or following or during any subsequent step as described below.

According to another variant of the invention the mixture obtained in the last step of the process described above can then undergo all the conceivable conversion steps in order to obtain a purified form. By "purified" is meant here that the mixture obtained at the end of the process as described above was subjected to at least one additional step aiming to enrich the mixture obtained with the protein-melanin complex according to the invention. In this respect a step of separation of the liquid and solid phases can be envisaged, for example by frontal or tangential filtration, such as for example filtration under vacuum or by passing through washed wool or by gravity such as for example sedimentation, flotation or centrifugation.

A concentration or one or more purification steps can be envisaged, advantageously intended to totally or partially remove the minerals and/or the reactional residues that may be present in the mixture, such as for example sulphates, any excess of copper or also sodium. The free sulphites may optionally be converted to sulphate before their removal by oxidation with active oxygen, in whatever form.

In this respect all the methods known in the prior art can be used. By way of example, separation by selective column chromatography can be mentioned, for example of ionic type. Advantageously, the components, reagent and/or solvent that are used can be of food quality. Membrane separation or separation by selective precipitation can also be mentioned.

This can be carried out by the use of chelating agents, such as ethylenediamine tetraacetic acid, or ion exchange resins, such as those containing iminodiacetic functional groups, and the use of isoelectric precipitation in order to separate the types of proteins. Ultrafiltration can be used in several steps of the procedure in order to improve the effectiveness of the removal of reagent or separation of the proteins.

Once purified, the product obtained at the end of the process which contains the bioassimilable protein-melanin complex according to the invention, advantageously the pure bioassimilable protein-melanin complex, can be dried by all methods known to a person skilled in the art such as for example drying by fluidized bed, spraying, lyophilisation or also by atomization. It is also possible if desired for additional steps of the grinding, mixing or other type, to be carried out in order to obtain a specific granulometry for the subsequent uses envisaged.

A person skilled in the art understands that it is during the last step that the protein-melanin complex according to the invention is constituted between the soluble peptide fraction and the melanin, so that the two fractions are perfectly homogenized and bound.

In fact, at this stage of the process, the peptide fraction can be bound by weak and ionic bonds to the melanin fraction rendered water-soluble in the reaction medium as soon as the latter is in suitable pH and temperature conditions, allowing it to be bound to the peptides. At this stage a person skilled in the art will know without difficulty how to adjust the pH and/or temperature conditions of the medium in order to obtain the protein-melanin complex according to the invention in the form that is desired. By way of example, it is possible to consider a pH range different from that of the pHi of the soluble proteins/peptides, ensuring the presence of a charge on the peptides in question facilitating their interaction with the melanin. In this option it is possible to consider a pH greater than the pHi over a range from 5 to 11, ideally over a range from 6 to 8.

For example, if in the first step of the process, oxidative sulphitolysis is used to render the protein fraction solubilizable, then the reaction medium will contain copper in the form of a cuproammonium complex. As this reaction medium is found at the end of the process, said cuproammonium complex will always be present at the end of the hydrolysis step. Under the operating conditions, the copper ions can establish ionic interactions on the melanin and protein fractions participating in obtaining a protein-melanin complex.

Moreover, in order to prevent any denaturation of the protein-melanin complex (precipitation, chemical modification etc.) all of the subsequent optional operations carried out with the aim of purifying and concentrating the complex may be carried out at a temperature that does not allow these degradations. Thus, the temperature for these operations may not exceed 100° C., preferentially 90° C., very preferentially 75° C., even for a very short period of time (few seconds to several hours).

The process according to the invention is a mild process, which allows a protein-melanin complex, advantageously a keratino/melanin complex, to be obtained without degradation of the melanin, and which allows a bioassimilable protein-melanin complex to be obtained having useful properties, advantageously biological properties, which make it possible to envisage its use in many fields and in many galenic forms. Among the remarkable properties of the bioassimilable protein-melanin complex according to the invention, its remarkable bioassimilation should be noted, making it possible to envisage the preparation of a formulation comprising said bioassimilable protein-melanin complex suitable for administration by oral route or by topical application route on the skin.

In addition to a remarkable bioassimilation, studies conducted by the inventors have made it possible to demonstrate that the bioassimilable protein-melanin complex according to the invention can be capable of stimulating melanogenesis, particularly at the level of the skin and/or the hair and/or the eyes, but also in the brain and in the inner ear canal. This property can make it possible to promote an increase in the pigmentation of the skin both with and without exposure to ultra-violet radiation, as well moreover a regeneration of the colouration of the keratinized appendages particularly of the bristles, the hair or also of the wool and a regeneration of the pigmentation of the eye. These properties can be used in animals, preferentially mammals, particularly man.

Thus, the bioassimilable protein-melanin complex according to the invention can be used for introducing exogenous melanin into the organism, by non-surgical route, particularly exogenous melanin that has retained its intrinsic properties.

The bioassimilable protein-melanin complex according to the invention can be used for the practical application of all the known properties of melanin.

Thus, a subject of the invention is also the use of the bioassimilable protein-melanin complex according to the invention for stimulating melanogenesis, particularly in the skin, in the keratinized appendages, in the hair, in the bristles, in the wool, in the eyes, in the brain and/or in the inner ear canal, preferentially in the hair, the bristles, the wool and/or the eyes.

Yet another subject of the invention is the use of the bioassimilable protein-melanin complex according to the invention for trapping free radicals, advantageously thus combating their harmful effects such as tissue aging, in particular the appearance of wrinkles and fine lines in the skin.

A subject of the invention is also the use of the bioassimilable protein-melanin complex according to the invention for increasing cell regeneration, elasticity and/or skin hydration, for reinforcing cell cohesion, particularly in the skin and/or the keratinized appendages.

This property of trapping free radicals can find another application in combating oxidative stress and therefore in the treatment or the prevention of its consequences such as many diseases for example cataracts, arthritis, cardio-vascular diseases or cancers.

Moreover, it is known that melanin can neutralize the harmful effects of radiation whether it is ionizing or not.

Thus, melanin may absorb a large amount of energy and is thought to produce only a small amount of heat when it absorbs this energy. Thus it has been suggested that melanin may absorb large amounts of energy of all kinds, including the energy from sunlight, X-ray machines, and the energy formed in the cells during the metabolism thereof.

Thus, a subject of the invention is also the use of the bioassimilable protein-melanin complex according to the invention for protecting living organisms from ionizing radiation ((far) ultraviolet radiation, X-rays, gamma rays, neutron, electron/$\beta^-$ particle, positron/$\beta^+$ particle, muon, proton, $^4$He ion/a particle, $^{12}$C ion) or non-ionizing radiation ((near) ultraviolet A, B and/or C, visible light, infrared A, B and/or C, microwaves, radio waves).

Preferentially, a subject of the invention is the use of the bioassimilable protein-melanin complex according to the invention for protecting living organisms from far or near ultraviolet radiation (A, B or C), visible light, infrared radiation (A, B and/or C) or also X-rays.

Moreover, melanin is known for fixing and concentrating heavy metals in the feathers of birds. It is therefore conceivable to use the bioassimilable protein-melanin complex according to the invention for trapping heavy metals, advantageously those of the organism, advantageously the human organism, and thus detoxifying said organism.

A subject of the invention is also the use of the bioassimilable protein-melanin complex according to the invention in the preparation of cosmetic, dermatological, pharmaceutical or also food compositions.

A subject of the invention is also a composition comprising at least one bioassimilable protein-melanin complex according to the invention. Said composition can be a cosmetic, dermatological, pharmaceutical or also a food composition, as a result of which in addition to the bioassimilable protein-melanin complex said composition can comprise any other compound and/or adjuvant usually used in the cosmetic, dermatology, pharmacy or food fields.

A particularly preferred composition according to the invention can comprise some of the bioassimilable protein-melanin complex according to the invention, tyrosine and/or cysteine, advantageously in the free or combined form or in the peptide form. This composition is particularly suitable as a food supplement.

According to the invention, said composition can comprise some of the bioassimilable protein-melanin complex in a quantity comprised between 1% and 100%, preferentially comprised between 20% and 95%, very preferentially comprised between 50% and 95% by weight with respect to the total weight of the composition.

This composition is particularly suitable for promoting melanogenesis.

Said composition may be in all galenic forms which are known and compatible with its use, particularly the form of a cream, a solution, an ointment, lotion, a soap, a foam, a shampoo, a deodorant, a make-up remover, a mascara, an eyeliner, a lipstick, a gel, a spray, these forms being more particularly suitable for a use for application on the skin and/or the hair or also in the form of a tablet, a syrup, an ingestible powder, a gelatin capsule, a soft capsule, a hard capsule, a chewing-gum, granules, a pre-mixture for food, a liquid preparation, a semi-solid preparation, these forms being more particularly suitable for a use by ingestion by route oral. Other more specific forms of use can be envisaged such as a vaginal preparation, a rectal preparation, an ocular preparation, medicated swabs or an impregnated dressing.

Of course these compositions can moreover comprise any other suitable compound or adjuvant in the chosen galenic form. In this respect anti-foaming agents, catalysts, filtration clarification agents/filtration adjuvants, bleaching agents, washing and peeling/shelling agents, plucking and peeling/depilation agents, ion exchange resins, contact freezing agents and cooling agents, desiccating/anticaking agents, enzymes, acidification, alkalinization or neutralization agents, stripping, flocculating and coagulating agents, decontamination agents, scale preventatives, extraction solvents, mineral, natural and expressed oils, chemically reactive substances, oxidants, vitamins, mineral salts, excipients, surfactants, preservatives, ultraviolet filters, dyes, antioxidants, alginates, sweeteners, flavour enhancers, waxes and hydrocarbons, chewing-gums, propellant gases, inertifiers, conditioners or tracers can be mentioned.

A subject of the invention is also the use of a composition according to the invention, for introducing exogenous melanin into the organism, by non-surgical route, particularly exogenous melanin having retained its intrinsic properties, or for stimulating melanogenesis, particularly in the skin, in the eyes or in the keratinized appendages, preferentially in the hair, the bristles, the wool, or for protecting living organisms from ultraviolet radiation, or for trapping free radicals, advantageously combating their harmful effects such as tissue aging, in particular the appearance of wrinkles and fine lines in the skin, or for combating oxidative stress and treating or preventing its consequences such as for example cataract, arthritis, cardio-vascular diseases or cancers or for neutralizing the potentially harmful effects of radiation other than UV radiation or for trapping heavy metals, advantageously those of the organism and thus detoxifying the organism or also for the preparation of a pharmaceutical composition intended for the prevention and/or the treatment of maculopathy (ARM) and/or of macular degeneration (ARMD).

FIG. 1: Diagram showing the experimentation areas used during the trials.

FIG. 2: Illustration of the variation in the parameters L* (2A) and ITA (2B) in the study of the effect of the food supplement comprising the bioassimilable protein-melanin complex (product), on the immediate cutaneous pigmentation (UVA exposure).

FIG. 3: Illustration of the variation in the melanic index (MI) in the study of the effect of the food supplement comprising the bioassimilable protein-melanin complex (product), on the immediate cutaneous pigmentation (UVA exposure).

FIG. 4: Illustration of the variations in the parameters L* (4A) and ITA° (4B) in the study of the effect of the food supplement comprising the bioassimilable protein-melanin complex (product), on the delayed pigmentation (UVB/UVA exposure).

FIG. 5: Illustration of the variations in the melanic index (MI) in the study of the effect of the food supplement comprising the bioassimilable protein-melanin complex (product), on the delayed pigmentation (UVB/UVA exposure).

FIG. 6: Illustration of the variation in the parameters L* (6A) and ITA° (6B) in the study of the effect of the food supplement comprising the bioassimilable protein-melanin complex (product), on an unexposed area.

FIG. 7: Illustration of the variation in the melanic index (MI) in the study of the effect of the food supplement comprising the bioassimilable protein-melanin complex (product), on an unexposed area.

FIG. 8: Illustration of the variation in the parameters L* in the study of the effect of the food supplement comprising the bioassimilable protein-melanin complex (product), on hair colour.

FIG. 9: Illustration of the results of the bioassimilability study of the elements of the protein-melanin complex according to the invention.

FIG. 10: Calibration curve established in order to determine the quantity of melanin present in the samples obtained at the end of the bioassimilability study.

FIG. 11: Illustration of the results of the study of the modification in the protein content of the skin for the protein-melanin complexes. [ ☐ Control, ■Active Group].

Other elements, characteristics and advantages of the invention will become apparent on reading the following examples given by way of illustration and with reference to the attached figures.

FIG. 1 illustrates the location of the areas of skin subjected to UV radiation during the trials presented in the examples. The presence should be noted of a measurement area of the Minimal Erythema Dose (MED) defined as the lowest dose of UltraViolet (UV) radiation causing the first perceptible erythema appearing on the major part of the UV exposure site, in the 16 to 24 hours after the exposure, and a measurement area of the minimal dose of persistent pigment darkening (MPPD) defined as the Minimal Persistent Pigment Darkening Dose (MPPD).

The different control areas 1A and 1B receive defined doses of UV (MED and MPPD) and make it possible to measure the epidermal response before taking the protein-melanin product.

The areas 2A, 3A and 4A make it possible to measure the epidermal response after taking the protein-melanin product under UVA every 10 days. This corresponds to the measurement of the immediate pigmentation due to the melanin which migrates to the surface of the skin in response to the UVA radiation.

The area 4B makes it possible to measure the epidermal response after taking the protein-melanin product and under UV A/B. This corresponds to the measurement of the delayed pigmentation due to the increased production of melanin measured after 30 days of treatment and which results in a more intense and persistent tan in response, which corresponds to the activation of the synthesis of the melanin (melanogenesis).

The area NE is the measurement area before and after taking the complex, without UV irradiation. This corresponds to research into the activity of the product on melanogenesis in the absence of irradiation.

FIG. 2 illustrates the results obtained in the study of the variation in the parameters L* (2A) and ITA° (2B) after administration of the food supplement comprising the bioassimilable protein-melanin complex (product), on the immediate cutaneous pigmentation (UVA exposure). It should be noted that on D0 two hours after one exposure to the UVA, the skin was significantly darker (reduction in the parameter L*; FIG. 2A) and more pigmented (reduction in the parameter ITA°; FIG. 2B) after the use of the food supplement comprising the bioassimilable protein-melanin complex (product) according to the invention.

This effect was observed from the 10th day of use of the product and the efficacy also increases with time (maximum effect observed after 30 days of use of the product: reduction of 225% in the parameter ITA° compared to before the use of the product). These results are statistically significant (p<0.001%).

FIG. 3 illustrates the results obtained in the study of the variation in the melanic index (MI) after administration of the food supplement comprising the bioassimilable protein-melanin complex (product), on the immediate cutaneous pigmentation (UVA exposure). It should be noted that after 10 days of use of the product, the measurements with the Mexameter showed the skin to be slightly more pigmented, two hours after the UVA exposure (+14%, variation at the limit of significance). After 20 and 30 days of use of the product, the increase in the melanic index is much greater and becomes statistically significant (on D30: +106%, p<0.001).

FIG. 4 illustrates the results obtained in the study of the variation in the parameters L* (4A) and ITA (4B) after administration of the food supplement comprising the bioassimilable protein-melanin complex (product), on the delayed pigmentation (UVB/UVA exposure). It should be noted that after 30 days of use of the food supplement comprising the bioassimilable protein-melanin complex (product), the measurements with the Spectrocolorimeter showed the skin to be significantly darker (reduction in the parameter L*) and more pigmented (reduction in the parameter ITA°) after one, two or three UVB/UVA exposures (after three exposures: significant reduction in the parameter ITA° of 206% compared to before the use of the product).

These results are statistically significant (p<0.001%).

FIG. 5 illustrates the results obtained in the study of the variation in the melanic index (MI) after administration of the food supplement comprising the bioassimilable protein-melanin complex (product), on the delayed pigmentation (UVB/UVA exposure). It should be noted that after 30 days of use of the food supplement comprising the bioassimilable protein-melanin complex (product), the measurements with the Mexameter showed a skin that is slightly more pigmented (increase in the melanic index) after one, two or three UVB/UVA exposures (after three exposures, increase in the melanic index of 217% compared to before use). These results are statistically significant (p<0.001%).

FIG. 6 illustrates the results obtained in the study of the variation in the parameters L* (6A) and ITA° (6B) after administration of the food supplement comprising the bioassimilable protein-melanin complex (product), on an unexposed area. It should be noted that during the entire period of taking the food supplement comprising the bioassimilable protein-melanin complex (product), the measurements with the Spectrocolorimeter have not shown a relevant variation in the colour of the skin on an area not exposed to UV: variations of 0% to 2%, which are not significant for the most part and not relevant from a biological point of view (not visible to the naked eye).

FIG. 7 illustrates the results obtained in the study of the variation in the melanic index (MI) after administration of the food supplement comprising the bioassimilable protein-melanin complex (product), on an unexposed area. It should be noted that between 10 and 39 days of use of the food supplement comprising the bioassimilable protein-melanin complex (product), the measurements with the Mexameter have shown a very slight increase in the melanic index (significant variation or at the limit of significance between 4% and 6%).

FIG. 8 illustrates the results obtained in the study of the variation in the parameters L* in the study of the effect of the food supplement comprising the bioassimilable protein-melanin complex (product), on hair colour. It should be noted that during 120 days of use of the food supplement comprising the bioassimilable protein-melanin complex (product), the measurements with the Spectrocolorimeter have shown a significantly darker hair colour (13% after 120 days of use, p<0.001). The effect increases with the treatment time. A variation in the shade of the hair was also observed with a colour that is less "yellow" and less "red".

FIG. 9 illustrates the results of the study of bioassimilability of the protein-melanin complex according to the invention. A bioassimilability of the proteins in the simulated gastro-intestinal liquids of 40.5±0.8%, a bioassimilability of the tyrosine equal to 1.85±0.2%, and a bioassimilability of melanin in the simulated gastro-intestinal fluids of 9.43±0.7% is noted.

The total bioassimilability of the protein-melanin complex was mathematically determined by adding the contents of proteins, tyrosine and melanin; the result is a value for the bioassimilability of the protein-melanin complex of 49.93% (FIG. 9).

Figure 1:
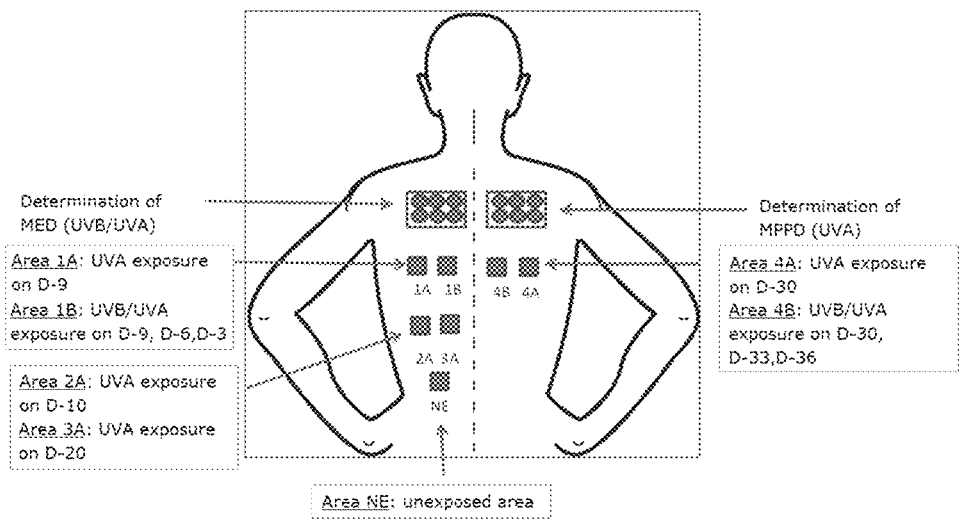

The protein content (cohesion) is measured by using the Corneofix foil method (Courage+Khazaka electronic GmbH).

The Corneofix® F 20 foils are applied onto the stratum corneum of a clean face on T0 and T90 days. Determination of the content of the proteins captured in the foils of the Corneofix® F 20 allows evaluation of skin cohesion.

An improvement in skin cohesion implies a reduction in the quantity of proteins captured in the foils between the samplings on days T0 and on T90.

Taking the protein-melanin complex significantly improved skin cohesion with respect to the control on day 90 with a reduction of 19.7% in the protein content with respect to the control ($P<0.001$).

EXAMPLE 1

Preparation of a Bioassimilable Protein-Melanin Complex According to the Invention First Step: Oxidative Sulfitolysis Applied to Wool
Procedure:
100 kg of washed degreased sheep's wool from the "Noire du Velay" breed is introduced into a tank.
Preparation of the Copper-Ammonium Solution and the Sulphites Solution:
Preparation of the Soluble Copper-Ammonium Hydroxide Solution in a Basic Medium:

In another tank, approximately 20 litres of an aqueous solution of ammonium hydroxide at 25% is mixed with 8 kg of pure copper, in the form of copper sulphate. Then approximately 750 litres of water is added, in which 50 kg of sodium sulphites has previously been dissolved.

Progress of the Reaction, Controlled Parameters:

The reaction mixture is added to the tank containing the wool then set in motion. The temperature is maintained between 20 and 40° C., and air is injected in order to provide oxygen. When the reaction medium has become sufficiently fluid the mixture is stirred. This operation is conducted for a duration of approximately 1 to 2 days, until the fibres have lost all mutual cohesion.
Second Step: Hydrolysis and Enzymatic Inactivation Then 350 g of the enzyme Protex 6L from Genencor or Multifect PR 6L from Brenntag (alkaline serine protease) is added the enzymatic activity of which is 580,000 U/g in the medium at a pH maintained between 9 and 10, and at a temperature comprised between 40 and 50° C.;

It is left to hydrolyze for 24 hours under stirring.

As hydrolysis proceeds, with the pH increasing, sodium hydroxide is added in order to maintain the pH constant between 9 and 10.

When the pH no longer varies, therefore it is no longer necessary to add sodium hydroxide, or when it is considered that the hydrolysis is sufficient, the hydrolysis step is then terminated.

The reaction medium then contains, among others, the protein-melanin complex that is the subject of the invention, which can be used as it is or purified and concentrated by any techniques known to a person skilled in the art.

EXAMPLE 2

Composition Comprising the Protein-Melanin Complex Obtained in Example 1

2A) lotion for slowing hair loss and restoring the colour to grey hair by topical application topic on the scalp and the hair of the head.

| | |
|---|---|
| Protein-melanin complex | 7.0 g |
| Urea | 1.0 g |
| Sodium lactate | 0.5 g |
| Phenoxyethanol | 0.1 g |
| Fragrance | qs |
| Water qsf | 100.0 g |

2B) preparatory cream for accelerating tanning and regenerating the epidermis

| | |
|---|---|
| Protein-melanin complex | 5.0 g |
| Glyceryl behenate | 2.0 g |
| Isononyl isononanoate | 3.0 g |
| Shea butter | 1.5 g |
| Glycerine | 4.0 g |
| Tocopherol | 0.1 g |
| Vaseline oil | 8.0 g |
| Polyglycerol ester | 0.5 g |
| Fragrance | qs |
| Glycerol undecylanate | 0.1 g |
| Water | qsf 100.0 g |

2C) Food supplement, preparatory to and accelerator of tanning, in capsule form

| | |
|---|---|
| Protein-melanin complex in microgranulated powder form | 325.0 mg |
| Vitamin C | 90.0 mg |
| Copper gluconate | 1.0 mg |
| Magnesium stearate | 2.0 mg |
| Silicon dioxide | 0.2 mg |
| 1 Hard gelatin capsule | 94.0 mg |

EXAMPLE 3

Evaluation of the Effect of a Bioassimilable Protein-Melanin Complex According to the Invention on Skin Pigmentation The objective of this study is to evaluate the effect of the bioassimilable protein-melanin complex according to the invention, prepared in Example 1, on skin pigmentation under UV stimulation, after use of the product studied for 10, 20 and 30 days.

The following were studied during this evaluation:
the effect of the product on skin pigmentation after exposure to UVA and measurement of the immediate pigmentation (2 hours after exposure) with a Spectrocolorimeter and a Mexameter after use of the product for 10, 20 and 30 days. This pigmentation mainly involves the activation of the melanin already present in the skin.
the effect of the product on skin pigmentation after repeated exposure to UV(B+A) and measurement of the delayed pigmentation with a Spectrocolorimeter and a Mexameter after 30 days' use of the product. This pigmentation mainly involves the synthesis of new melanin.

3.1) Tools and Protocols

UV Exposures

In order to measure the Minimal Erythema Dose (MED: the lowest dose of UltraViolet (UV) radiation causing the first perceptible erythema appearing on the major part of the UV exposure site), in the 16 to 24 hours after the exposure and the Minimal Persistent Pigment Darkening Dose (MPPD), a Xenon lamp of the Solar Light Multiport 601-300W type, equipped with a WG320 (1.25 mm) filter for the UV(A+B) and a WG335 (3 mm) filter (UVA) for eliminating the UVB with a power rating of 300 W was used.

The spectra emitted are from 290 to 400 nm for the UV (A+B) and from 320 to 400 nm for the UVA.

A UG11 (1 mm) filter and dichroic mirror were used to eliminate infra-red radiation and visible light.

The skin surface exposed is delimited using a mask comprising six holes (diameter 8 mm) 0.5 cm$^2$.

In order to determine the MED the UV flux of each optical fibre is adjusted by the technician in order to obtain a geometrical progression of 15%. The system is used with a constant flux, all the fibres are open at the same time.

In order to determine the MPPD the UVA flux of each optical fibre is determined by the technician in order to obtain a geometric progression of 25%. The system is used with a constant flux, all the fibres are open at the same time.

For the exposures to UV (A+B) and UVA, a Xenon lamp of the Solar Light Monoport 1000W High Power Solar Simulator—Model LS1000 type, having a UVA (A+B) spectrum from 290 to 400 nm and UVA spectrum from 320 to 400 nm was used. The skin surface exposed is 4×4 cm at maximum.

Measurements With the Spectrophotometer at the Level of the Skin

The colorimetric measurement of the skin is carried out using a Spectrocolorimeter MINOLTA CM700-d, equipped with an 8 mm diameter head.

The Spectrocolorimeter converted the colours situated within the range of human perception into a numerical code comprising three parameters:

L*: represents lightness (from dark to pale), a*: represents the range from the greens to the reds, b*: represents the range from the blues to the yellows.

a* and b* are chrominance parameters and L* is a luminance parameter.

It then becomes possible to express, in the smallest detail, the differences between two skin areas which appear to be of the same colour. After calibration, the measurements are carried out directly on the skin using a pulsed Xenon light source and a double beam system for measuring the light emitted and correcting any slight deviation.

This instrument is commonly used in cosmetics and in medicine for measuring the colour of the skin.

The parameters L* (characteristic of lightness) and b* (characteristic of cutaneous melanin yellow pigmentation) are studied during an investigation of cutaneous pigmentation.

These two parameters are utilized through calculation of the "Individual Typological Angle" (ITA), which defines the degree of pigmentation of the skin of a person by incorporating the lightness (L*) and the melanization parameter (b*), according to the following formula:

$$ITA° = [\text{Arc tan}((L*-50)/b*)] \times 180/\pi$$

The higher the ITA, the lighter the skin.

Each measurement is the average of three acquisitions.

Measurements With the Mexameter at the Level of the Skin

The Mexameter is an instrument from Courage and Khazaka, equipped with a 5 mm diameter head, which particularly measures the melanin and haemoglobin content of skin. These two components are mainly responsible for the colour of the skin.

The measurement is based on the absorption principle. The special probe of the Mexameter MX18 emits light at three predefined wavelengths (568 nm (green), 660 nm (red) and 880 nm (infrared)). A photo-detector measures the light reflected by the skin. This measurement is based on the same optical principle which consists of measuring the light absorbed and reflected at the red and infrared wavelengths for melanin.

A Melanic Index (Mx) is calculated from the intensity of the light absorbed and reflected at 600 and 880 nm respectively.

An Erythema Index (Ex) is calculated from the intensity of the light absorbed and reflected at 568 and 660 nm respectively.

Only the Melanic Index, which represents the melanin content of the skin, was analyzed. An increase in this parameter characterizes an increase in skin pigmentation.

Progress of the Test

The test was carried out on 35 subjects

On D-10

The subjects come to the laboratory without having applied any product on their backs since the previous evening and the areas of exposure on their backs are defined as shown in FIG. 1

UVB/UVA exposure for determining the MED.

UVA exposure for determining the MPPD.

2 hours after UVA exposure: reading the MPPD

On D-9

The subjects come to the laboratory without having applied any product on their backs since the previous evening.

Between 16 and 24 hours after UVB/UVA exposure: reading the MED.

Measurements with the Spectrocolorimeter on areas 1A, 1B and NE.

Measurements with the Mexameter on areas 1A, 1B and NE.

UVB/UVA exposure on area 1B at 0.8 MED.

UVA exposure on area 1A at 1.25 MPPD.

2 hours after UVA exposure: measurements with the Spectrocolorimeter and Mexameter on area 1A.

On D-6

The subjects come to the laboratory without having applied any product on their backs since the previous evening.

Measurements with the Spectrocolorimeter and Mexameter on areas 1B and NE.

UVB/UVA exposure on area 1B at 0.8 MED.

On D-3

The subjects come to the laboratory without having applied any product on their backs since the previous evening.

Measurements with the Spectrocolorimeter and Mexameter on areas 1B and NE.
UVB/UVA exposure on area 1B at 0.8 MED.
On D0
The subjects come to the laboratory without having applied any product on their backs since the previous evening.
Measurements with the Spectrocolorimeter and Mexameter on areas 1B and NE.
The product is taken at a rate of 2 capsules per day, in the morning with breakfast, until the end of the trial.
On D10
The subjects come to the laboratory without having applied any product on their backs since the previous evening.
Measurements with the Spectrocolorimeter and Mexameter on areas 2A and NE.
UVA exposure on area 2A at 1.25 MPPD.
2 hours after UVA exposure: measurements with the Spectrocolorimeter and Mexameter on area 2A.
On D20
The subjects come to the laboratory without having applied any product on their backs since the previous evening.
Measurements with the Spectrocolorimeter and Mexameter on areas 3A and NE.
UVA exposure on area 3A at 1.25 MPPD.
2 hours after UVA exposure: measurements with the Spectrocolorimeter and Mexameter on area 3A.
On D30
The subjects come to the laboratory without having applied any product on their backs since the previous evening.
Measurements with the Spectrocolorimeter on areas 4A, 4B and NE.
Measurements with the Mexameter on areas 4A, 4B and NE.
UVB/UVA exposure on area 4B at 0.8 MED.
UVA exposure on area 4A at 1.25 MPPD.
2 hours after UVA exposure: measurements with the Spectrocolorimeter and Mexameter on area 4A.
On D33
The subjects come to the laboratory without having applied any product on their backs since the previous evening.
Measurements with the Spectrocolorimeter and Mexameter on areas 4B and NE.
UVB/UVA exposure on area 4B at 0.8 MED.
On D36
The subjects come to the laboratory without having applied any product on their backs since the previous evening.
Measurements with the Spectrocolorimeter and Mexameter on areas 4B and NE.
UVB/UVA exposure on area 4B at 0.8 MED.
On D39
The subjects come to the laboratory without having applied any product on their backs since the previous evening.
Measurements with the Spectrocolorimeter and Mexameter on areas 4B and NE.

Analysis of the Data

Statistical analysis of the data makes it possible to determine the significance of the variations under the effect of the tested product.

The comparison is based on the values obtained at the different evaluation times.

The test used is the Student's t-test on paired data. The application conditions are the random and simple nature of the samples and the normality of the population of differences.

The principle of the test is to pose a null hypothesis (H0) of an absence of difference between the average effect at different evaluation times ($\bar{d}=0$) and an alternative hypothesis H1 (our research hypothesis) of a difference between the evaluation times ($\bar{d}<>0$).

The probability p of observing a difference between the times which is at least as great as that observed if the null hypothesis is true is then determined.

If p≥5%, the null hypothesis is rejected. The alternative hypothesis H1 of a significant difference between the evaluation times is therefore accepted.

If p>5%, the null hypothesis is accepted. The data have not revealed a significant difference between the evaluation times.

3.2) Results

In the tables shown below, the results for L* are dark to light data, the results for ITA° are data ranging from more pigmented to less pigmented.

3.2.1) Effect of the Food Supplement Comprising the Bioassimilable Protein-Melanin Complex (Product) on Immediate Skin Pigmentation (UVA Exposure)

Spectrocolorimeter

A summary of the results is shown in Table 1 below.

TABLE 1

| | D 10 | | | D 20 | | | D 30 | | |
|---|---|---|---|---|---|---|---|---|---|
| | Variation | | | Variation | | | Variation | | |
| | AU | % | p | AU | % | p | AU | % | p |
| L* | −2.4 +/− 0.3 | 118 | <0.001 | −3.9 +/− 0.4 | 189 | <0.001 | −6.1 +/− 0.4 | 248 | <0.001 |
| ITA° | −2.6 +/− 0.4 | 82 | <0.001 | −6.2 +/− 0.4 | 161 | <0.001 | −7.2 +/− 0.5 | 225 | <0.001 |

AU: average +/− SEM

Figure 2A:
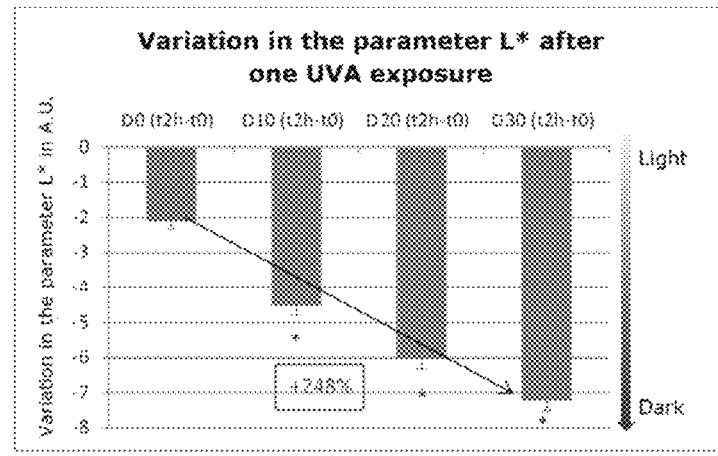
Figure 2B:
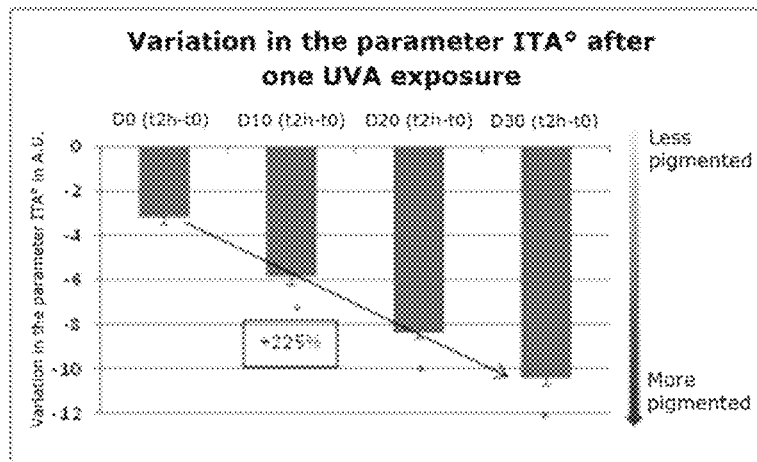

These results are also illustrated in FIGS. 2A and 2B.

Two hours after a UVA exposure, the skin was significantly darker (decrease in the parameter L*) and more pigmented (decrease in the parameter ITA°) after the use of the food supplement comprising the bioassimilable protein-melanin complex (product) according to the invention.

This effect was observed from use of the product for 10 days and the effectiveness also increases over time (maximum effect observed after use of the product for 30 days: decrease of 225% in the parameter ITA° compared to before use of the product.)

Mexameter

A summary of the results is shown in Table 2 below.

TABLE 2

|  | D 10 | | | D 20 | | | D 30 | | |
| --- | --- | --- | --- | --- | --- | --- | --- | --- | --- |
|  | Variation | | | Variation | | | Variation | | |
|  | AU | % | p | AU | % | p | AU | % | p |
| MI | 3.3 +/− 1.8 | 14 | 0.076 | 20 +/− 1.9 | 84 | <0.001 | 25.3 +/− 3.6 | 106 | <0.001 |

MI = Melanic Index;
AU: average +/− SEM

Figure 3:
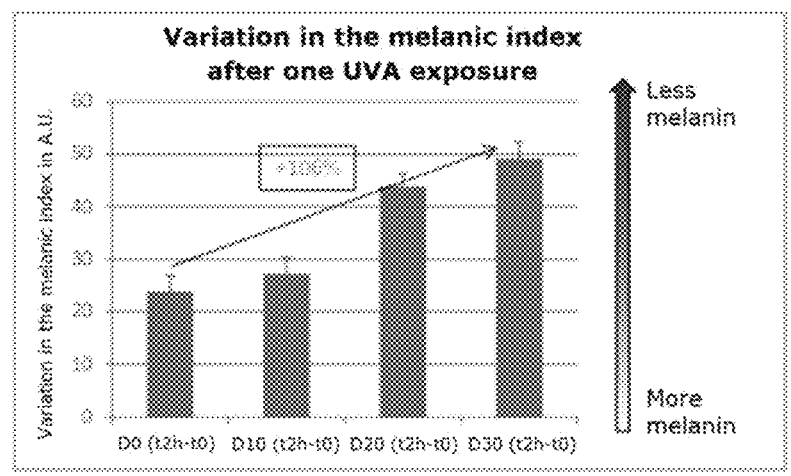

These results are also illustrated in FIG. 3.

After use of the product for 10 days, the measurements with the Mexameter showed a slightly more pigmented skin two hours after the UVA exposure (+14%, variation at the limit of significance). After use of the product for 20 and 30 days, the increase in the Melanic Index is much greater and becomes statistically significant (at D30: +106%, p<0.001).

3.2.2) Effect of the Food Supplement Comprising the Bio-assimilable Protein-Melanin Complex (Product) on Delayed Pigmentation (UVB/UVA Exposure)

Spectrocolorimeter

A summary of the results is shown in Table 3 below.

TABLE 3

|  |  | D 30 | | |
| --- | --- | --- | --- | --- |
|  |  | Variations | | |
|  |  | AU | % | p |
| After 1 exposure to UV | L* | −2.2 +/− 0.0 | 170 | <0.001 |
|  | ITA° | −4.2 +/− 0.3 | 190 | <0.001 |
| After 2 exposures to UV | L* | −4.1 +− 0.3 | 180 | <0.001 |
|  | ITA° | −6.7 +/− 0.6 | 166 | <0.001 |
| After 3 exposures to UV | L* | −7.0 +/− 0.3 | 249 | <0.001 |
|  | ITA° | −11.0 +/− 0.5 | 206 | <0.001 |

Figure 4A:
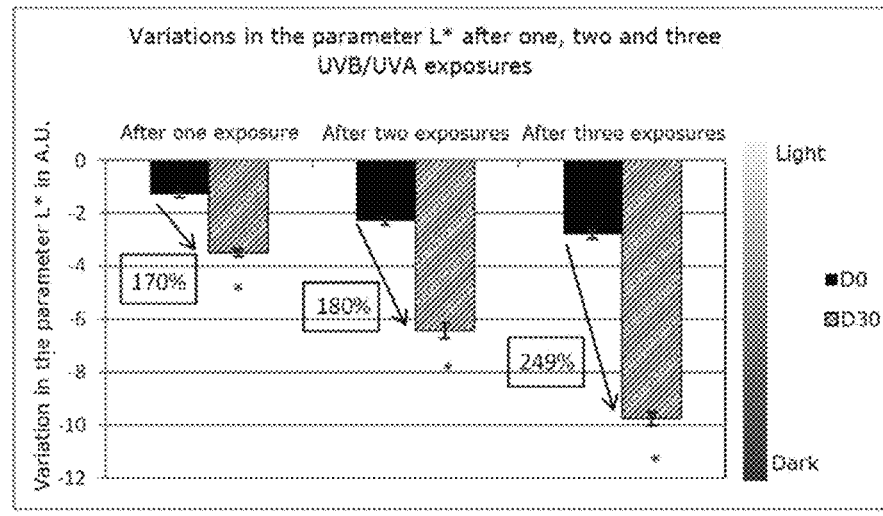
Figure 4B:
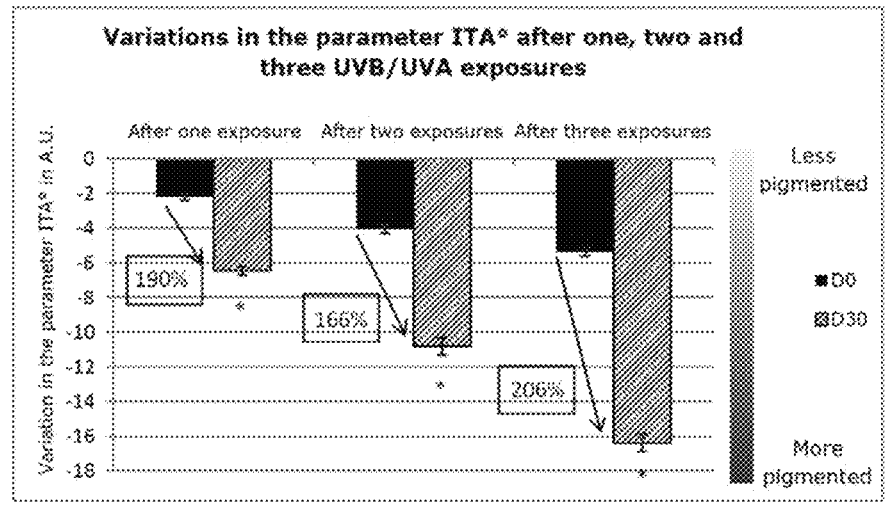

These results are also illustrated in FIGS. 4A and 4B.

After use of the food supplement comprising the bioassimilable protein-melanin complex (product) for 30 days, the measurements with the Spectrocolorimeter showed a significantly darker (decrease in the parameter L*) and more pigmented (decrease in the parameter ITA°) skin after one, two or three UVB/UVA exposures (after three exposures: significant decrease in the parameter ITA° of 206% compared to before the use of the product).

Mexameter

A summary of the results is shown in Table 4 below.

TABLE 4

|  |  | D 30 | | |
| --- | --- | --- | --- | --- |
|  |  | Variations | | |
|  |  | AU | % | p |
| MI | After 1 exposure to UV | 15.1 +/− 0.0 | 193 | <0.001 |
|  | After 2 exposures to UV | 26.5 +− 1.9 | 167 | <0.001 |
|  | After 3 exposures to UV | 43.1 +/− 2.7 | 217 | <0.001 |

MI = Melanic Index;
AU: average +/− SEM

Figure 5:
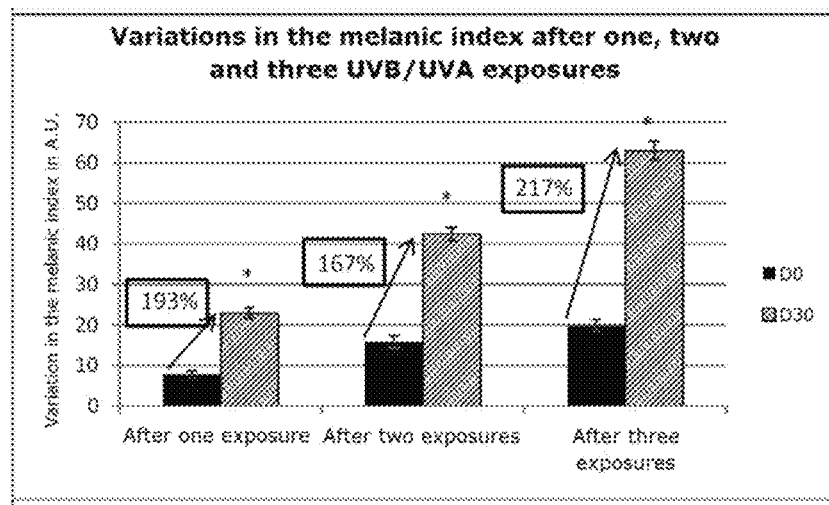

These results are also illustrated in FIG. 5.

After use of the food supplement comprising the bioassimilable protein-melanin complex (product) for 30 days, the measurements with the Mexameter showed a significantly more pigmented skin (increase in the melanic Index) after one, two or three UVB/UVA exposures (after three exposures, increase in the melanic Index of 217% compared to before use).

3.2.3) Effect of the Food Supplement Comprising the Bio-assimilable Protein-Melanin Complex (Product), on an Unexposed Area Spectrocolorimeter A summary of the results is shown in Table 5 below.

TABLE 5

|  | L* | | | b* | | | ITA° | | |
| --- | --- | --- | --- | --- | --- | --- | --- | --- | --- |
|  | Variation | | | Variation | | | Variation | | |
|  | AU | % | p | AU | % | p | AU | % | p |
| D 10 | 0.6 +/− 0.2 | 1 | 0.004 | 0.5 +/− 0.2 | 2 | 0.010 | 0.3 +/− 0.2 | 1 | 0.139 |
| D 20 | 0.1 +/− 0.2 | 0 | 0.604 | 0.0 +/− 0.2 | 0 | 0.804 | 0.0 +/− 0.0 | 0 | 0.000 |
| D 30 | 0.1 +/− 0.2 | 0 | 0.722 | −0.1 +/− 0.2 | −1 | 0.552 | 0.0 +/− 0.0 | 0 | 0.000 |
| D 33 | 0.1 +/− 0.2 | 0 | 0.549 | −0.1 +/− 0.2 | 0 | 0.689 | 0.0 +/− 0.0 | 0 | 0.000 |
| D 36 | 0.0 +/− 0.2 | 0 | 0.975 | −0.2 +/− 0.2 | −1 | 0.358 | 0.0 +/− 0.0 | 0 | 0.000 |
| D 39 | 0.1 +/− 0.2 | 0 | 0.613 | −0.1 +/− 0.2 | 0 | 0.714 | 0.0 +/− 0.0 | 0 | 0.000 |

AU: average +/− SEM

Figure 6A:
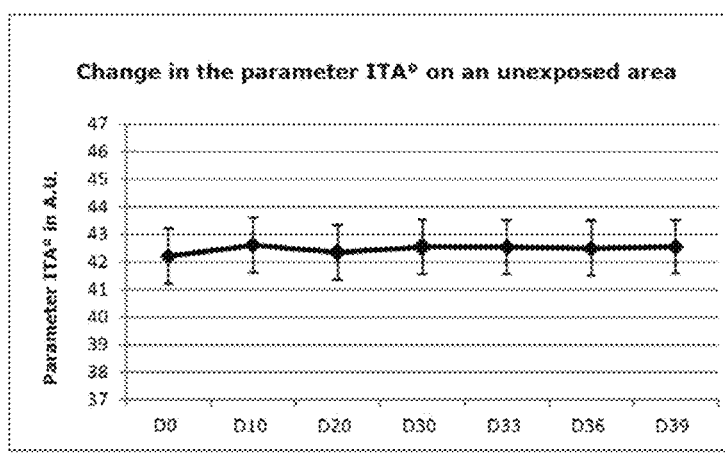
Figure 6B:
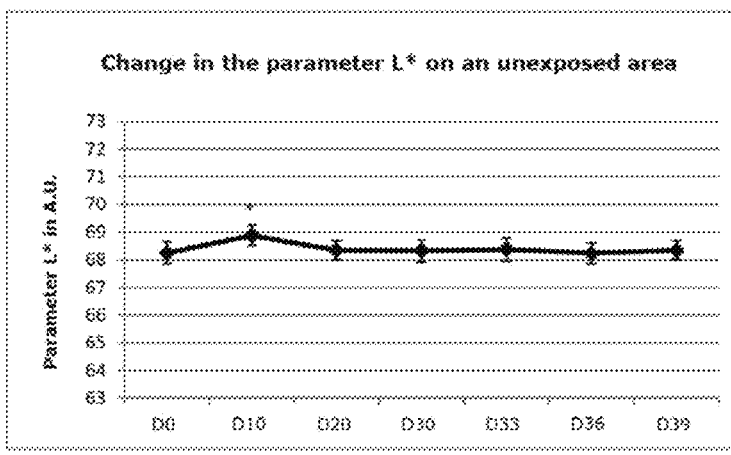

These results are also illustrated in FIGS. 6A and 6B.

At no time while the food supplement comprising the bioassimilable protein-melanin complex (product) was being taken did the measurements with the Spectrocolorimeter show a relevant variation in the colour of the skin on an area not exposed to UV: variations of 0% to 2%, not significant for the majority and not relevant from the biological point of view (not visible to the naked eye).
Mexameter A summary of the results is shown in Table 6 below.

TABLE 6

|      | Variation    |   |       |
|------|--------------|---|-------|
|      | AU           | % | p     |
| D 10 | 3.0 +/− 1.3  | 5 | 0.027 |
| D 20 | 2.7 +/− 1.4  | 5 | 0.064 |
| D 30 | 3.4 +/− 1.4  | 6 | 0.020 |
| D 33 | 3.3 +/− 1.2  | 6 | 0.011 |
| D 36 | 2.1 +/− 1.2  | 4 | 0.088 |
| D 39 | 3.1 +/− 1.2  | 5 | 0.014 |

AU: average +/− SEM

Figure 7:
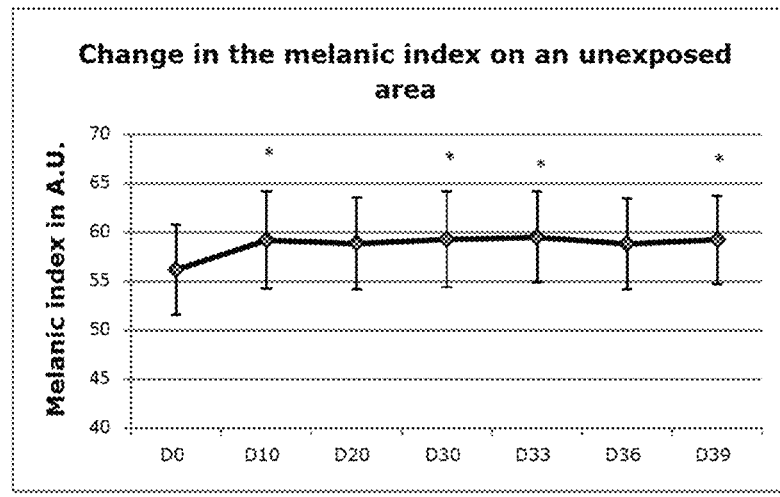

These results are also illustrated in FIG. 7.

After use of the food supplement comprising the bioassimilable protein-melanin complex (product) for 10 to 39 days, the measurements with the Mexameter showed a very slight increase in the melanic index (significant variation or at the limit of significance between 4% and 6%).

3.3) Conclusion

The main objective of this test was to assess the effect of the food supplement comprising the bioassimilable protein-melanin complex (product) on skin pigmentation under UV stimulation, after use of the tested product for 0, 20 and 30 days.

Under the conditions of this test, the food supplement comprising the bioassimilable protein-melanin complex (product) tested:

allowed a significant improvement in the immediate pigmentation 2 hours after a UVA exposure. This effect was observed both with the Spectrocolorimeter and with the Mexameter, from use for 10 days. The effectiveness of the product also increased after use for 30 days.
  An increase in the pigmentation was observed of 225% with the Spectrocolorimeter and of 106% with the Mexameter.
  allowed a significant improvement in the delayed pigmentation after one, two or three UVB/UVA exposures. This effect was observed both with the Spectrocolorimeter and with the Mexameter, from use of the product for 30 days. After 3 UVB/UVA exposures, an increase in the pigmentation was observed of 206% with the Spectrocolorimeter and of 217% with the Mexameter.
  caused a very slight increase in the Melanic Index on an area not exposed to UV (variation of 4% to 6%). This effect was observed from use of the product for 10 days.

It is noteworthy that the product was greatly liked by the majority of the subjects. 66% of the subjects found their skin to have more colour and 76% wished to continue to use the product. The product has moreover been well tolerated by the sample group of testers. No sensation of discomfort or intolerance has been reported by the subjects.

EXAMPLE 4

Evaluation of the Effect of a Bioassimilable Protein-Melanin Complex According to the Invention on the Pigmentation of the Hair The objective of this study is to evaluate the effect of the bioassimilable protein-melanin complex according to the invention, prepared in Example 1, on the pigmentation of the hair.

The study was conducted with 32 volunteers with grey and/or salt-and-pepper hair and applying no dye for the duration of the study.

Measurements of the hair colour are carried out using a Chromametre® on D0, D60, D90 and D120 in order to evaluate the effect of the product on the pigmentation of the hair.

4.1) Measurements with the Chromametre® on the Hair

On D0, the hair was shaved over a mini-area of 1 $cm^2$ in order to perfectly locate the measurements during the entire study. This mini-area was identified in the CRF using centimetric measurements.

Four colorimetric measurements were carried out on the root of the hair surrounding the shaved mini-area (up, down, to the left and to the right) using a MINOLTA CR-400 Chromametre® MINOLTA CR-400, equipped with an 8 mm diameter head. Analysis of the data was carried out on the average of four measurements.

At the following kinetic time, the mini-area was identified and shaved again if necessary and the measurements were carried out with the Chromametre® as explained above.

The Chromametre® converts the colours situated in the range of human perception into a numerical code comprising three parameters:

L*: represents the lightness (from dark to pale),
  a*: represents the range from the greens to the reds,
  b*: represents the range from the blues to the yellows.

a* and b* are the parameters of chrominance and L* a parameter of luminance.

It then becomes possible to express, in the smallest details, the differences between two areas which appear to be the same colour. After calibration, the measurements are carried out directly on the hair using a pulsed Xenon light source and a double beam system for measuring the light emitted and correcting any slight deviation.

This instrument is commonly used in cosmetics and in medicine for measuring the colour of the skin or the hair.

4.2) Progress of the Trial

On D0:
  The subjects come to the laboratory without having applied any product on the hair since the previous evening.
  Definition and shaving of a mini-area of 1 $cm^2$ on the scalp.
  Measurements with the Chromametre® on the root of the hair around this mini-area. Four measurements are carried out up, down, to the left and to the right of the area.

On D60, D90, D120:
  The subjects come to the laboratory without having applied any product on the hair since the previous evening.
  Location of the mini-area defined on D0. This area is shaved again.

Measurements with the Chromametre® on the root of the hair around this mini-area. Four measurements are carried out up, down, to the left and to the right of the area.

4.3) Analysis of the Data

Statistical analysis of the data makes it possible to determine the significance of the variations under the effect of the tested product.

The comparison is based on the values obtained at the different evaluation times.

The test used is the Student's t-test on paired data. The application conditions are the random and simple nature of the samples and the normality of the population of differences.

The principle of the test is to pose a null hypothesis (H0) of absence of difference between the average effect at different evaluation times ($\bar{d}=0$) and an alternative hypothesis H1 (our research hypothesis) of a difference between the evaluation times ($\bar{d} < > 0$).

The probability p of observing a difference between the times which is at least as great as that observed if the null hypothesis is true is then determined.

If p≥5%, the null hypothesis is rejected. The alternative hypothesis H1 of a significant difference between the evaluation times is therefore accepted.

If p>5%, the null hypothesis is accepted. The data have not made it possible to demonstrate a significant difference between the evaluation times.

4.4) Results

Chromametre®

A summary of the results is shown in Table 7 below.

Pepsin Digestion.

A quantity of 100 mg of melanoprotein complex according to the invention was mixed with 1.0 mL of a 0.85 N solution of hydrochloric acid (HCl).

24,000 U of porcine pepsin per mL were then added and the sample was incubated in a water bath at 39° C. for 120 min.

Pancreatin Digestion.

At the end of the pepsin digestion, the samples were transferred into dialysis tubes 18 cm long and 1.3 mL of a 0.8 M solution of $NaHCO_3$ containing 22.60 mg of porcine pancreatin/mL (8×USP) were added to pepsin digesta. The dialysis tubes were sealed at each end with clips. The dialysis tubes with a porosity greater than 12,000 and with a diameter of 1.6 cm (Sigma Chemical Co., reference D6191) were placed in a 250 mL flask containing 100 mL of 0.05 M succinate buffer. The samples were incubated at 39° C. under stirring at 120 cycles per minute for 4 h.

After incubation of the pancreatin, the components available in the dialysis medium were determined by different experimental procedures.

All the experiments were carried out in triplicate and the results are expressed as the average of the results of the 3 experiments.

Quantitative Determination of the Proteins by the Lowry Method 1 mL of each sample was mixed with 4.5 mL of Lowry reagent (9.8 mL of $Na_2CO_3$ (2% W/V), 0.1 mL of $CuSO_4$-$5H_2O$ (1% W/V) and 0.1 mL of $Na^+$—$K^+$ tartrate (0.5% W/V). The solution was mixed and incubated for 10 min. Then 0.5 mL of Folin-Ciocalteau reagent 1N was added and

TABLE 7

| | J60 | | | J90 | | | J120 | | |
|---|---|---|---|---|---|---|---|---|---|
| | Variation | | | Variation | | | Variation | | |
| | A.U. | % | p | A.U. | % | p | A.U. | % | p |
| L* | −2.2 +/− 0.3 | −4 | <0.001 | −4.9 +/− 0.4 | −9 | <0.001 | −7.5 +/− 0.5 | −13 | <0.001 |
| a* | −0.5 +/− 0.2 | −8 | 0.012 | −1.4 +/− 0.2 | −22 | <0.001 | −2.4 +/− 0.2 | −37 | <0.001 |
| b* | −0.6 +/− 0.1 | −6 | <0.001 | −1.3 +/− 0.2 | −14 | <0.001 | −2.0 +/− 0.2 | −22 | <0.001 |

AU: average +/− SEM

Figure 8:
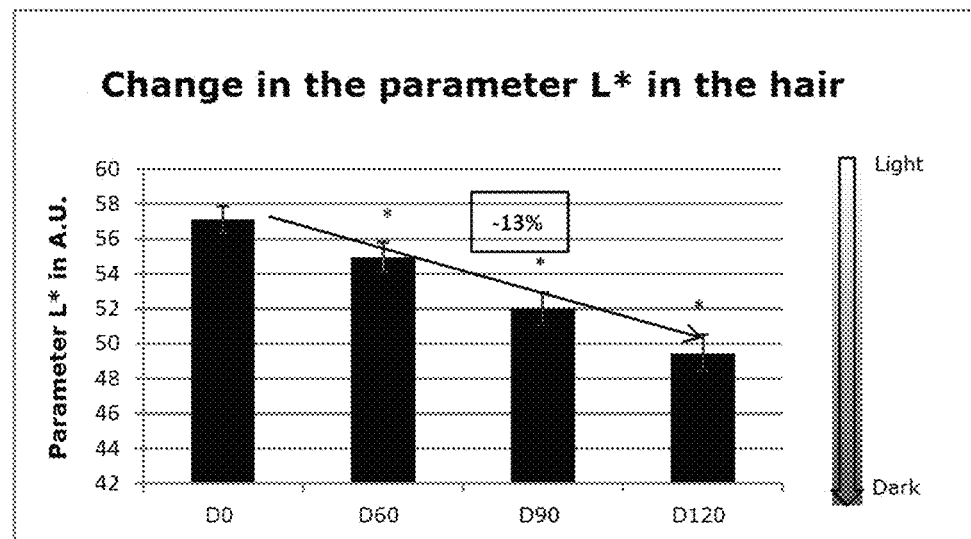

These results are also illustrated in FIG. 8.

After use of the food supplement comprising the bioassimilable protein-melanin complex (product) for 30, 90 and 120 days, the measurements with the Chromametre® showed a significantly darker hair colour (13% after use for 120 days, p<0.001). The effect increases with the treatment time. A variation of the shade of the hair was also observed with a colour that is less "yellow" and less "red".

EXAMPLE 5

Study of the Bioassimilability of the Protein-Melanin Complex According to the Invention Experimental System Evaluation of the bioassimilability of the protein-melanin complex according to the invention and of the different components of said complex in the simulated gastric and intestinal fluids was studied following the dialysis tube procedure [D. W. BOLLINGER et al.; J. Agric. Food Chem.; 2005. 53: 3287-3294].

left to react for 30 min. Finally, the absorbance was measured at 660 nm [O. H. LOWRY et al.; J. Biol. Chem.; 1951. 193: 265-275].

The data are expressed in percentage of available proteins.

Quantitative Determination of the Tyrosine by HPLC

The HPLC system consisted of a Jasco BIP-je pump, a Rheodyne 7725 injector (230 µL loop), and a Jasco UVDEC-100 V UV detector.

A C8 type column (0.4×15 mm) packed with particles 5 µm in size was used for the determination. The separation was monitored at 210 nm. A mobile phase constituted by an acetonitrile-water mixture (5:95 v/v) was used. The flow rate was maintained at 1.5 mL $min_{-1}$ Identification of the peaks was carried out by comparing the retention time of the samples with a standard solution of tyrosine.

The data are expressed in percentage of available tyrosine.

Quantitative Determination of Melanin by Spectrophotometric Methods

After the incubations of pepsin and pancreatin, the quantity of available melanin was determined by spectrophotometry using a Jasco V-530 UV/V is spectrometer, according to the method developed by Ozeki and his collaborators

[Ozeki, H., et al.; 1996. Spectrophotometric characterization of eumelanin and pheomelanin in hair. *Pigment Cell Research* 9:265-270 or Ozeki, H. et al.; 1995. Chemical characterization of hair melanins in various coat-color mutants of mice. *Journal of Investigative Dermatology* 105:361-366], method slightly modified by the inventors.

The samples obtained after the pepsin and pancreatin digestions were dried under vacuum and the residue was redissolved in Soluene-350 (Perkin Elmer), a strong organic base formulated with toluene. The samples were analysed in order to determine the absorbances at 500 nm (A500). The A500 values correspond to the total melanin contained in the sample.

Figure 10:
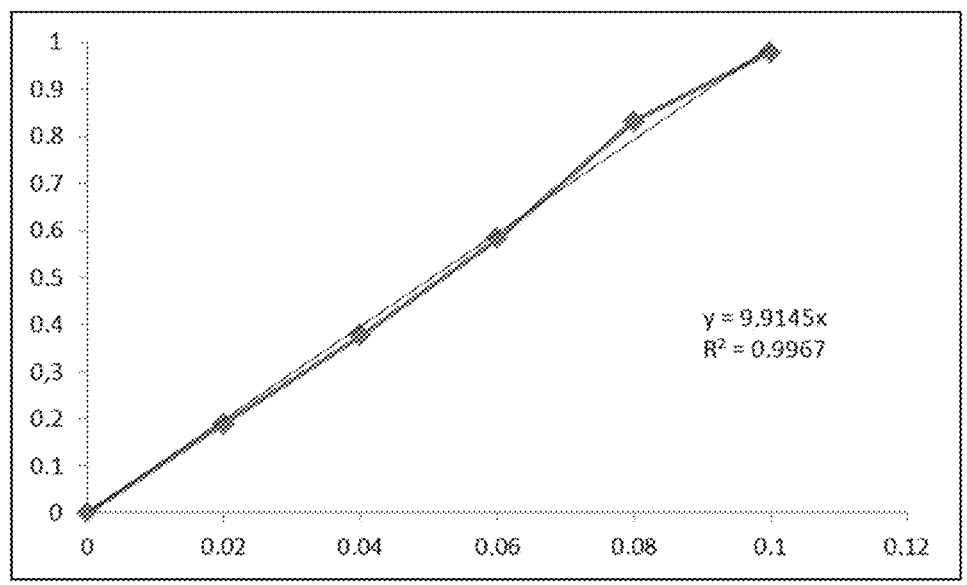
FIG. 10 shows the curve used for the quantitative determination of melanin by spectrophotometric methods (see Example 5).

The total concentrations of melanin were calculated with reference to a calibration curve established from five different standard solutions of melanin (0.02, 0.04, 0.06, 0.08 and 0.10 mg/ml) in Soluene-350 (see FIG. 10). The absorbance of the standard solutions was measured at 500 nm in order to establish a calibration curve and the correlation coefficient (R2), slope and the y-axis intercept of the regression equation obtained were calculated by the least squares method.

The absorbance values of the melanic samples obtained by the bioavailability studies in vitro carried out in triplicate, and the corresponding bioavailability percentages, are shown in Table 8 below.

TABLE 8

| Abs | Bioavailability (%) |
|---|---|
| 0.7535 | 8.92 |
| 0.7832 | 9.31 |
| 0.8526 | 10.06 |

The final in vitro value of the bioavailability (9.43±0.68%) was calculated as the average of the data obtained by the three experiments carried out (Table 1)

The data are expressed as a percentage of available melanin.

Results

Figure 9:
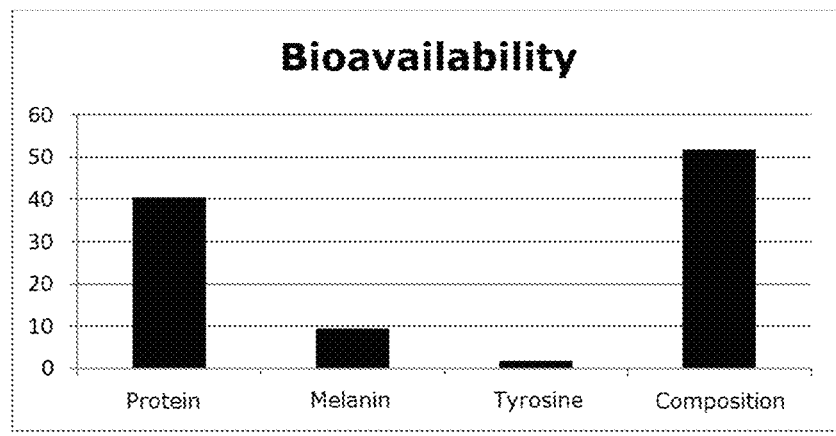

The results are presented in FIG. 9

The method using dialysis tubes is a rapid and low cost method for evaluating the bioassimilability of different types of compounds.

As explained previously, the components of the protein-melanin complex are determined by using different experimental procedures.

More precisely, for the quantification of the content of proteins in the gastro-intestinal digesta, the Lowry assay was used.

A bioassimilability of the proteins in the simulated gastro-intestinal liquids of 40.5±0.8% was measured.

The quantification of tyrosine was carried out by HPLC analysis by comparing the chromatograms of the samples to that of a standard solution of tyrosine.

A bioassimilability equal to 1.85±0.2% was thus determined.

Finally, the bioassimilability of melanin in the simulated gastro-intestinal fluids was determined by spectrophotometric analysis.

A bioassimilability equal to 9.43±0.7% was thus determined.

The total bioassimilability of the protein-melanin complex was mathematically determined by adding the content of proteins, tyrosine and melanin; the result is a bioassimilability value of the protein-melanin complex of 49.93 (FIG. 9).

EXAMPLE 5

Evaluation of the Effect of a Bioassimilable Protein-Melanin Complex According to the Cell Cohesion in the Human Skin Measurement of the protein content of the skin makes it possible to evaluate the cohesion of the cells.

Evaluation of skin cohesion as a function of its protein content is useful for evaluating the effectiveness of the cell cohesion due to the treatment received by the subjects of the study. A reduction in the quantity of proteins exuded on the surface of the skin reflects an increase in the cell cohesion.

The protein content (cohesion) is measured by using the Corneofix foil method with the Corneofix® F 20 kit (Courage+Khazaka electronic GmbH), according to the supplier's protocol. The non-invasive samples of 10 layers of the stratum corneum of a clean face were thus obtained in order to determine the protein content.

The Lowry method (Oliver H. Lowry, Nira J. Rosebrough, A Lewis Farr and Rose J. Randall, "Protein measurement with the Folin phenol reagent", *J. biol. Chem.*, vol. 193, n° 1, 1951, p. 265-275) is used for measuring the protein content. It is based on the ability of copper to bind to proteins under alkaline conditions, and when the Folin reagent is added, a complex is formed with the protein which is visible at 550 nm.

The subjects are divided into 2 groups, a control group and a so-called "active" group.

The "active" group [■] received 500 mg/day in 1 dose of melanoprotein complex according to the invention for 90 days.

The "control" group [ ☐ ] received 500 mg/day in 1 dose of maltodextrin for 90 days.

The subjects of the control group (not having received this protein-melanin complex according to the invention), showed no improvement in the protein content of the skin from the base line on day 90. The subjects having received the protein-melanin complex according to the invention, improved the protein content of their skin significantly on day 90 compared to the base line. Up to less than 15.9% of proteins captured in the Corneofix® F 20 foils (P<0.001 was noted.

Taking the protein-melanin complex also significantly improved the protein content of the skin compared to the control on day 90 with a difference of 19.7% compared to the control (P<0.001).

95.8% of the subjects of the active group showed an improvement in skin cohesion.

Figure 11:
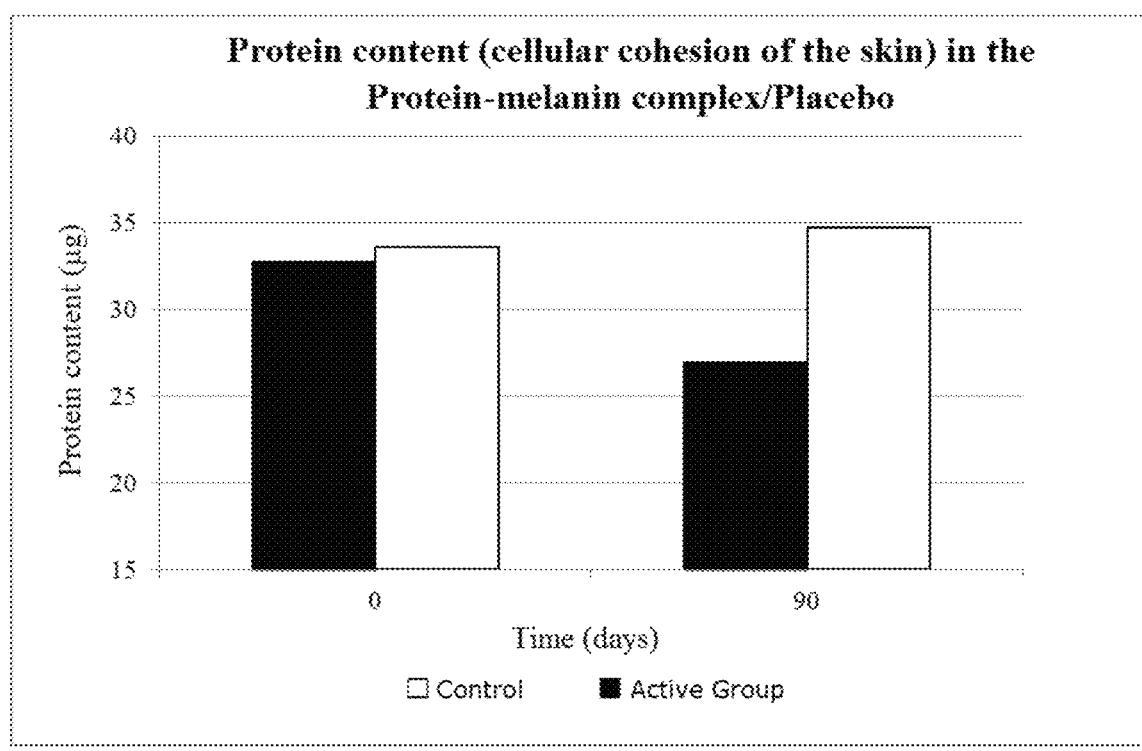
FIG. 11 illustrates the results of the change in the protein content of the skin collected from subjects having received the protein-melanin complex according to the invention [■Active Group] compared to a group of subjects not having received said protein-melanin complex [☐ontrol].

The results of this study are shown in FIG. 11.

The invention claimed is:

1. A bioactive bioassimilable protein-melanin complex, comprising at least one protein extract, and melanin, wherein the protein of the protein extract comprises at least one cysteine; and wherein the at least one cysteine is chemically modified with a sulphite group grafted to the sulphur atom of said at least one cysteine.

2. The protein-melanin complex according to claim 1, wherein said protein extract is soluble in water from 0.1 to 99%.

3. The protein-melanin complex according to claim 1, wherein the complex comprises between 0.01% and 99.99% of protein extract.

4. The protein-melanin complex according to claim 1, wherein the complex comprises between 0.01% and 99.99% of melanin.

5. The protein-melanin complex according to claim 1, wherein the protein extract comprises peptides with a length between 2 and 1,000 amino acids.

6. The protein-melanin complex according to claim 1, wherein said protein extract and/or said melanin originate from different or identical protein and melanin sources, taken separately or originating from the same source.

7. The protein-melanin complex according to claim 1, wherein said protein extract and/or said melanin source is selected from the group consisting of wool, bristles, hair, claws, horns, feathers, plants, fruits, the ink from cephalopods, bacteria and a synthetic source.

8. The protein-melanin complex according to claim 1, wherein said protein extract and/or said melanin wool source is selected from the group consisting of sheep, mouflons, goats, chamois, takin, ibexes, Siberian ibexes, thars, Himalayan thars, serows, goral, musk ox, urial, bharal, isard, rabbits, hares, pikas, llama, alpaca, guanaco, vicuna, camel, dromedary, yak and feathers.

9. The bioactive protein-melanin complex according to claim 1, wherein said protein extract and/or said melanin originate from black sheep wool.

10. A composition, comprising the protein-melanin complex of claim 1.

11. The composition according to claim 10, which is in galenic form selected from the group consisting of a powder, a liquid, a cream, a lotion, a patch, and a spray.

12. A process for the preparation of the bioactive bioassimilable protein-melanin complex of claim 1, comprising a first step of rendering the protein water soluble by chemically modifying at least one cysteine of the protein by grafting a sulphite group to the sulphur atom of the at least one cysteine; and a second step comprising fractionating the protein and adding melanin in order to obtain a mixture comprising the protein-melanin complex.

13. The process according to claim 12, wherein the second step of fractionating is selected from the group consisting of acid hydrolysis, basic hydrolysis, enzymatic hydrolysis, and by partial oxidation using peracetic acid, hydrogen peroxide or an equivalent.

14. A method for preparing a cosmetic, dermatological, pharmaceutical or food composition, comprising preparing the cosmetic, dermatological, pharmaceutical or food composition with at least one bioactive bioassimilable protein-melanin complex according to claim 1.

15. A process for stimulating melanogenesis, comprising administering to a subject in need thereof an effective amount of the bioactive bioassimilable protein-melanin complex of claim 1.

16. The process according to claim 15, wherein melanogenesis is stimulated in the skin, the hair, the bristles, the wool, the keratinized appendages, the brain, the inner ear canal, and/or the eyes.

* * * * *